United States Patent [19]

Forster et al.

[11] Patent Number: 4,540,827
[45] Date of Patent: Sep. 10, 1985

[54] PHENOXYBENZENE DERIVATIVES

[75] Inventors: Heinz Forster, Wuppertal; Ludwig Eue, Leverkusen; Robert Schmidt, Bergisch-Gladbach, all of Fed. Rep. of Germany

[73] Assignee: Bayer Aktiengesellschaft, Leverkusen, Fed. Rep. of Germany

[21] Appl. No.: 616,355

[22] Filed: Jun. 1, 1984

Related U.S. Application Data

[62] Division of Ser. No. 513,933, Jul. 14, 1983, Pat. No. 4,482,736, which is a division of Ser. No. 318,899, Nov. 6, 1981, Pat. No. 4,435,208.

[30] Foreign Application Priority Data

Nov. 28, 1980 [DE] Fed. Rep. of Germany ....... 3044810

[51] Int. Cl.$^3$ ................. C07C 47/546; C07C 43/263; C07C 79/35; C07C 79/36
[52] U.S. Cl. .................................... 568/442; 568/586
[58] Field of Search ................................ 568/442, 586

[56] References Cited

U.S. PATENT DOCUMENTS 4,263,227 4/1981 Krass ..................... 564/256
4,306,900 12/1981 Swithenbank et al. ............. 568/586

FOREIGN PATENT DOCUMENTS 0107016 7/1974 Fed. Rep. of Germany .
2333848 1/1975 Fed. Rep. of Germany .
3017795 11/1980 Fed. Rep. of Germany .

Primary Examiner—Bernard Heflin
Attorney, Agent, or Firm—Sprung, Horn, Kramer & Woods

[57] ABSTRACT

Herbicidally active compounds of the formula

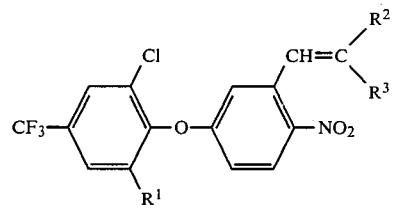

in which
$R^1$ represents a hydrogen or chlorine atom,
$R^2$ represents a hydrogen atom, a cyano group, an optionally substituted radical selected from alkyl, aryl, alkanoyl, benzoyl, alkoxycarbonyl, alkenoxycarbonyl, alkinoxycarbonyl, aralkoxycarbonyl and aryloxycarbonyl, or a radical of the general formula —COOM, in which
M represents a hydrogen atom, one equivalent of an alkali metal ion or alkaline earth metal ion or optionally substituted ammonium, and
$R^3$ represents a cyano group or a radical of the general formula

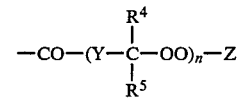

wherein
Y represent an oxygen or sulphur atom or an imino (NH) or alkylimino (Nalkyl) group,
$R^4$ and $R^5$ independently of each other represent a hydrogen atom or a methyl group,
n is 0 or 1 and
Z represents an optionally substituted radical.

Novel intermediates therefor are also shown.

3 Claims, No Drawings

PHENOXYBENZENE DERIVATIVES

This is a division of application Ser. No. 513,933, filed July 14, 1983, and now U.S. Pat. No. 4,482,736, which is a division of Ser. No. 318,899, filed Nov. 6, 1981, and now U.S. Pat. No. 4,435,208.

The present invention relates to certain new substituted phenoxycinnamic acid derivatives, to a process for their production, and to their use as herbicides. The invention further relates to novel intermediate products for the preparation of these substituted phenoxycinnamic acid derivatives, and to several processes for the synthesis of the intermediate products.

It is known that certain substituted diphenyl ethers can be used for combating weeds (see R. Wegler, Chemie der Pflanzenschutz- und Schädlingsbekämpfungsmittel (Chemistry of Plant Protection Agents and Pesticides), volume 5, pages 73 to 80, Springer-Verlag Berlin, Heidelberg, New York 1977).

The action of the compounds from the series of the diphenyl ethers which were previously known as herbicides is however unsatisfactory for many purposes.

The present invention now provides, as new compounds, substituted phenoxycinnamic acid derivatives of the general formula

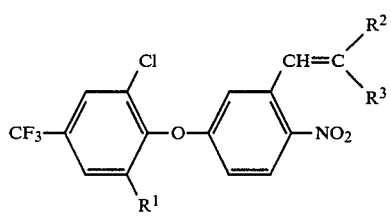

in which
R$^1$ represents a hydrogen or chlorine atom,
R$^2$ represents a hydrogen atom, a cyano group, an optionally substituted radical selected from alkyl, aryl, alkanoyl, benzoyl, alkoxycarbonyl, alkenoxycarbonyl, alkinoxycarbonyl, aralkoxycarbonyl and aryloxycarbonyl, or a radical of the general formuls —COOM,
in which
M represents a hydrogen atom, one equivalent of an alkali metal ion or alkaline earth metal ion or optionally substituted ammonium, and
R$^3$ represents a cyano group or a radical of the general formula

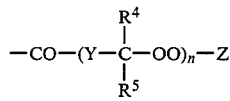

wherein
Y represents an oxygen or sulphur atom, or an imino (NH) or alkylimino (N-alkyl) group,
R$^4$ and R$^5$ independently of each other represent a hydrogen atom or a methyl group,
n is 0 or 1 and
Z represents an optionally substituted radical selected from alkyl, aralkyl, aryl, alkoxy, alkenoxy, alkinoxy, aralkoxy and aryloxy, or represents a radical of the general formula OM', in which M' independently of M, has any of the meanings given above for M, or
Z furthermore also represents the radical of the general formula

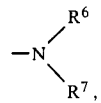

wherein
R$^6$ and R$^7$ independently of each other represent an optionally substituted radical selected from alkyl, cycloalkyl, alkenyl, alkinyl, aralkyl and aryl or, together with the N atom to which they are bonded, form an optionally substituted saturated or unsaturated, optionally benzo-fused, monocyclic or bicyclic structure, which optionally contains 1 to 3 additional N atoms or an oxygen atom or sulphur atom as hetero atom or atoms.

According to the present invention we further provide a process for the production of a compound of formula (I) of the present invention characterized in that a substituted phenoxybenzaldehyde of the general formula

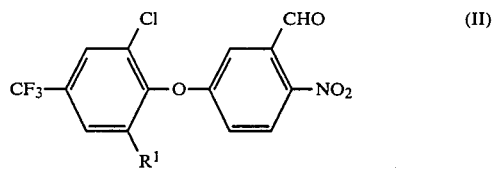

in which R$^1$ has the abovementioned meaning, is reacted with a methylene compound of the general formula

in which R$^2$ and R$^3$ have the abovementioned meanings, if appropriate in the presence of a catalyst and, if appropriate, in the presence of a diluent, and, if desired, the compound of the formula (I), which is thus formed, is converted into another compound of the formula (I) by modifying the radicals R$^2$ and/or R$^3$.

The novel phenoxycinnamic acid derivatives of the formula (I) of the present invention are distinguished by an excellent herbicidal activity and exhibit good selectivity in various crops such as soy beans, corn and cereals. In addition to their high activity against broad-leaved weeds, the compounds according to the invention also show a good activity against grasses, especially against species of millet; furthermore, when used after emergence, they exhibit plant growth-regulating, especially growth-inhibiting, properties and can be used, for example, as cotton defoliants.

Surprisingly, the phenoxycinnamic acid derivatives according to the present invention exhibit a substantially better herbicidal action than compounds which are known from the prior art and which have an analogous structure and the same type of action.

Preferred phenoxycinnamic acid derivatives according to the present invention are those in which $R^1$ represents a hydrogen or chlorine atom, $R^2$ represents a hydrogen atom, a cyano, $C_1$ to $C_4$ alkyl or acetyl radical, an optionally $C_1$ to $C_4$ alkyl-, $C_1$ to $C_4$ alkoxy-, halogen-, cyano- and/or nitro-substituted phenyl or benzoyl radical, a ($C_1$ to $C_4$ alkoxy)-carbonyl, ($C_3$ to $C_5$ alkenoxy)-carbonyl, ($C_3$ to $C_5$ alkinoxy)-carbonyl, phenyl-($C_1$ and $C_2$ alkoxy) carbonyl or phenoxy-carbonyl radical or a radical of the general formula COOM, in which M represents a hydrogen atom, a sodium or potassium cation, one equivalent of a magnesium or calcium cation, or ammonium which optionally contains 1 to 4 alkyl radicals with 1 to 4 carbon atoms, of which radicals 2 optionally jointly form a ring, and $R^3$ represents a cyano group or a radical of the general formula

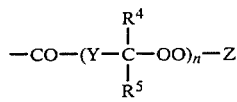

in which

Y represents a oxygen or sulphur atom or an imino (NH) or methylimino (NCH$_3$) group, $R^4$ and $R^5$ independently of each other represent a hydrogen atom or a methyl group n is 0 or 1 and Z represents a $C_1$ to $C_4$ alkyl or phenyl- $C_1$ or $C_2$ alkyl radical, an optionally $C_1$ to $C_4$ alkyl-, $C_1$ to $C_4$ alkoxy-, halogen-, cyano- and/or nitro-substituted phenyl radical, a $C_1$ to $C_4$ alkoxy, $C_3$ to $C_5$ alkenoxy, $C_3$ to $C_5$ alkinoxy, phenyl-$C_1$ or $C_2$ alkoxy or phenoxy radical or a radical of the general formula OM', in which M', independently of M, has any of those meanings given immediately above for M, or Z furthermore represents the radical of the general formula

in which $R^6$ represents a $C_1$ to $C_5$ alkyl, cyanoethyl, methoxyethyl, $C_3$ to $C_5$ alkenyl, $C_3$ to $C_5$ alkinyl, $C_3$ to $C_6$ cycloalkyl or phenyl-$C_1$ or $C_2$ alkyl radical and $R^7$ represents a $C_1$ to $C_5$ alkyl, cyanoethyl, methoxyethyl, $C_3$ to $C_5$ alkenyl, $C_3$ to $C_5$ alkinyl, $C_3$ to $C_6$ cycloalkyl, phenyl-$C_1$ or $C_2$ alkyl or phenyl radical, which is optionally substituted by $C_1$ to $C_4$ alkyl, $C_1$ to $C_4$ alkoxy, halogen, trifluoromethyl, cyano and/or nitro, or wherein the radicals $R^6$ and $R^7$, together with the nitrogen atom to which they are bonded, form an optionally methyl- and/or ethyl-substituted radical selected from pyrrolidyl, piperidyl, morpholinyl, indolyl, indolinyl, perhydroindolyl, 1,2,3,4-tetrahydroquinolyl, 1,2,3,4-tetrahydroisoquinolyl, perhydroquinolyl, perhydroisoquinolyl and perhydroazepinyl.

Particularly preferred compounds of the present invention are those in which $R^1$ represents a hydrogen or chlorine atom, $R^2$ represents a hydrogen atom, a cyano, $C_1$ to $C_4$ alkyl, acetyl or $C_1$ to $C_4$ alkoxycarbonyl radical and $R^3$ represents a cyano or ($C_1$ to $C_4$ alkoxy)-carbonyl radical or a radical of the general formula

—COOM wherein M represents a sodium or potassium cation or one equivalent of a magnesium or calcium cation.

If, in the process according to the invention, 5-(2-chloro-4-trifluoromethyl-phenoxy)-2-nitro-benzaldehyde and dimethyl malonate are used as starting materials, the course of the reaction can be represented by the following equation:

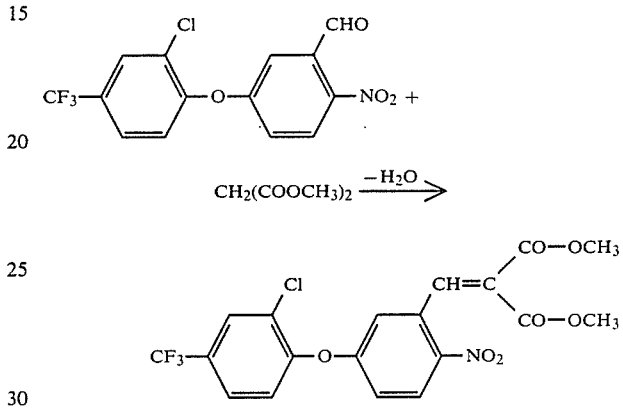

The formula (II) provides a definition of the phenoxybenzaldehydes to be used as starting materials in the process according to the invention.

Examples which may be mentioned are 5-(2-chloro-4-trifluoromethyl-phenoxy)-2-nitro-benzaldehyde and 5-(2,6-dichloro-4-trifluoromethyl-phenoxy)-2-nitrobenzaldehyde.

The phenoxybenzaldehydes of the formula (II) have not previously been described in the literature.

Accordingly the present invention further provides, as new compounds the phenoxybenzaldehydes of the formula (II), as defined above.

The present invention also provides a process for the production of a compound of formula (II), characterized in that (a) a phenoxybenzaldehyde-acylal of the general formula

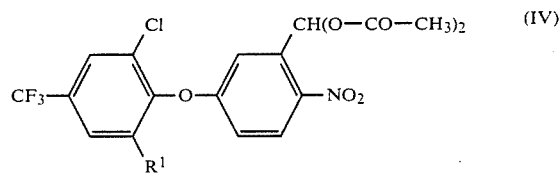

in which $R^1$ represents a hydrogen or chlorine atom, is reacted with an aqueous alkali metal hydroxide solution (such as a sodium hydroxide solution) if appropriate in the presence of an additional diluent, (such as methanol) and if appropriate at a temperature between 10° and 80° C., the mixture may then be diluted with water and the crystalline product of the formula (II) isolated by filtration, or (b) a phenoxybenzyl alcohol of the general formula

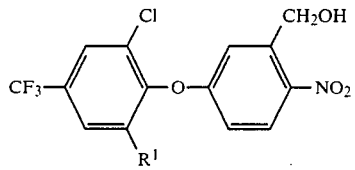

in which R¹ represents hydrogen or chlorine, is reacted with an oxidizing agent (such as nitric acid) in the presence of a diluent (such as water and nitromethane), generally at a temperature between 10° and 80° C., the mixture may then be diluted with water, and the crystalline product of the formula (II) isolated by filtration.

As examples of the acylals of the formula (IV) to be employed in preparation variant (a), there may be mentioned 5-(2-chloro-4-trifluoromethyl-phenoxy)-2-nitro-benzaldehyde-diacetacylal and 5-(2,6-dichloro-4-trifluoromethyl-phenoxy)-2-nitro-benzaldehyde-diacetacylal.

The acylals of the formula (IV) have not previously been described in the literature.

According to the present invention we therefore further provide, as new compounds, the acylals of the formula (IV) as defined above.

The present invention further provides a process for the production of an acylal of the formula (IV), characterized in that a phenoxybenzaldehyde of the general formula

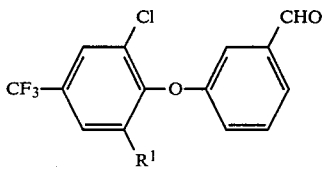

in which R¹ represents a hydrogen or chlorine atom, is reacted with acetic anhydride, if appropriate in the presence of a diluent (such as methylene chloride) generally at a temperature between 10° and 80° C., nitric acid is then added generally at a temperature between −10° and +20° C., after completion of the reaction the mixture may be diluted with water, the non-aqueous diluent, where present, separated off or distilled off, and the product of the formula (IV), obtained in crystalline form, isolated by filtration.

As examples of the phenoxybenzaldehydes of the formula (VI) there may be mentioned 3-(2-chloro-4-trifluoromethyl-phenoxy)-benzaldehyde and 3-(2,6-dichloro-4-trifluoromethyl-phenoxy)-benzaldehyde.

The phenoxybenzaldehydes of the formula (VI) have not previously been described in the literature.

According to the present invention we therefore further provide, as new compounds, phenoxybenzaldehydes of the formula (VI) as defined above.

The present invention also provides a process for the production of a phenoxybenzaldehyde of formula (VI) characterized in that 3-hydroxy-benzaldehyde is reacted with 3,4-dichloro- or 3,4,5-trichloro-benzotrifluoride in the presence of an acid-binding agent (such as potassium methylate) and in the presence of a diluent (such as dimethylsulphoxide and toluene), generally at a temperature between 50° and 120° C. Working up can be effected in accordance with customary methods, for example by distilling off the volatile components, digesting the residue with toluene, filtering, washing the residue and concentrating the filtrate. The residue thus obtained essentially contains the product of the formula (VI), which can be purified via its bisulphite adduct.

As examples of the phenoxybenzyl alcohols of the formula (V) to be employed in reaction variant (b) for the preparation of the compounds of the formula (II), there may be mentioned 5-(2-chloro-4-trifluoromethyl-phenoxy)-2-nitro-benzyl alcohol and 5-(2,6-dichloro-4-trifluoromethyl-phenoxy)-2-nitro-benzyl alcohol.

The phenoxybenzyl alcohols of the formula (V) have not previously been described in the literature.

According to the present invention we therefore further provide, as new compounds, phenoxybenzyl alcohols of formula (V), as defined above.

The present invention also provides a process for the production of a phenoxybenzyl alcohol of formula (V) characterized in that a phenoxybenzoic acid chloride of the general formula

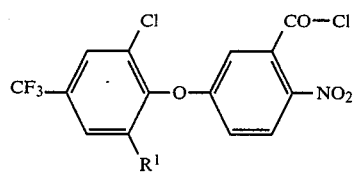

in which R¹ represents a hydrogen or chlorine atome, is reacted with a hydride complex (such as sodium boranate) in the presence of a diluent (such as diglycol dimethyl ether (diglyme)), generally at a temperature between −20 and +20 C.

Working up can be carried out in the usual manner, for example by diluting the mixture with water, acidifying it, for example with acetic acid, and isolating the product of the formula (V), which is obtained in a crystalline form, by filtration.

As examples of the phenoxybenzoic acid chlorides of the formula (VII) there may be mentioned 5-(2-chloro-4-trifluoromethyl-phenoxy)-2-nitro-benzoic acid chloride and 5-(2,6-dichloro-4-trifluoromethyl-phenoxy)-2-nitrobenzoic acid chloride.

The phenoxybenzoic acid chlorides of the formula (VII) are known (see DE-OS (German Published Specification) No. 2,950,401).

A compound of the formula (VII) is obtained when a phenoxybenzoic acid of the general formula

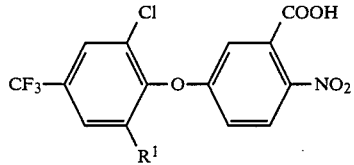

in which R¹ represents a hydrogen or chlorine atom, is reacted with a chlorinating agent (such as thionyl chloride) if appropriate with use of a catalyst (such as dimethylformamide) and, if appropriate, with use of a diluent (such as 1,2-dichloroethane) at a temperature between 10° and 100° C., and thereafter volatile components are distilled off under reduced pressure.

The phenoxybenzoic acids of the formula (VIII), namely 5-(2-chloro-4-trifluoromethyl-phenoxy)-2-nitrobenzoic acid and 5-(2,5-dichloro-4-trifluoromethylphenoxy)-2-nitrobenzoic acid, are already known (see U.S. Pat. No. 3,928,416).

Preferred methylene compounds of formula (III) also to be used as starting materials in the process according to the invention for the preparation of the phenoxycinnamic acid derivatives of the formula (I) are those in which $R^2$ and $R^3$ represent those radicals which have already been mentioned in connection with the description of the preferred and particularly preferred compounds of the formula (I).

As examples of the compounds of the formula (III) there may be mentioned malonic acid, its sodium potassium, calcium and magnesium salt, and its methyl ester, ethyl ester, n- and iso-propyl ester, n-, iso-, sec.- and tert.-butyl ester, malonodinitrile, cyanoacetic acid, its sodium, potassium, calcium and magnesium salt and its methyl ester, ethyl ester, n- and iso-propyl ester, n-, iso-, sec.- and tert.-butyl ester, and acetoacetic acid methyl ester, ethyl ester, n- and iso-propyl ester and n-, iso, sec.- and tert.-butyl ester.

The compounds of the formula (III) are known.

From a compound of the formula (I), in which $R^3$ represents a carboxyl or alkoxycarbonyl radical, it is possible to prepare another compound of the formula (I), in which $R^3$ represents the radical of the general formula

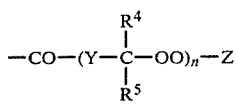

in which $R^4$, $R^5$, Y, Z and n have the abovementioned meanings, where necessary after conversion to the corresponding carboxylic acid chloride, by reaction with a compound of the general formula

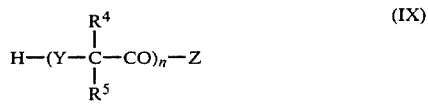

in which $R^4$, $R^5$, Y, Z and n have the abovementioned meanings, in accordance with customary methods, if appropriate in the presence of an acid-binding agent and, if appropriate, in the presence of a diluent.

As further possible ways of interconverting the compounds of the formula (I) formed by the process according to the invention there may be mentioned:

(1) decarboxylation, which in general takes place in situ, without isolation of the corresponding primary products, if malonic acid or cyanoacetic acid is used as a starting material;

(2) salt formation, for example by reaction of the corresponding acid with a basic alkali metal compound or alkaline earth metal compound; and (3) esterification, for example by reaction of the corresponding acid with an alcohol in the presence of a base (such as diazabicycloundecene) or by reaction with a suitable alkyl halide.

Details of the process for the preparation of the novel phenoxycinnamic acid derivatives of the formula (I) are given below. The process is generally carried out in the presence of a catalyst. Compounds which are suitable for accelerating condensation reactions between aldehydes and activated methylene compounds (aldol condensations) are used for this purpose. Preferably, aliphatic, aromatic or heterocyclic amines (such as tri-methylamine, triethylamine, pyrrolidine, piperidine, dimethylaniline, dimethylbenzylamine, diazabicyclooctane, diazabicyclononene, diazabicycloundecene and pyridine) are used, where appropriate as salts of weak acids (such as of acetic acid). The catalysts also include aminocarboxylic acids (such as β-alanine). Some of these catalysts, such as pyridine, can also advantageously be used as diluents.

Virtually any of the inert organic solvents can be used as diluents. They include, in particular, aliphatic and aromatic, optionally halogenated, hydrocarbons (such as pentane, hexane, heptane, cyclohexane, petroleum ether, petrol, ligroin, benzene, toluene, xylene, methylene chloride, ethylene chloride, chloroform, carbon tetrachloride, chlorobenzene and o-dichlorobenzene), ethers (such as diethyl ether and dibutyl ether, glycol dimethyl ether and diglycol dimethyl ether, tetrahydrofuran and dioxane), ketones (such as acetone, methyl ethyl ketone, methyl isopropyl ketone and methyl isobutyl ketone), esters (such as methyl acetate and ethyl acetate), nitriles (such as acetonitrile and propionitrile), amides (such as dimethylformamide, dimethylacetamide and N-methylpyrrolidone) and also dimethylsulphoxide, tetramethylenesulphone and hexamethylphosphorotriamide.

The reaction temperature can be varied within a substantial range. In general, the reaction is carried out at a temperature between 0° and 200° C., preferably between 20° and 150° C.

The process according to the invention is in general carried out under normal pressure.

In carrying out the process according to the invention, between 0.9 and 1.5 mol, preferably between 1.0 and 1.2 mol, of methylene compound of the formula (III) are employed per mol of phenoxybenzaldehyde of the formula (II).

To carry out the process according to the invention, the procedure followed in general is to bring the reactants of the formulae (II) and (III), as well as the catalyst and the diluent, together at room temperature and then to stir the mixture at an elevated temperature, preferably at between 50° and 120° C., until completion of the reaction. The water formed in the reaction is removed, where necessary, via a water separator.

Working up can be effected in accordance with customary methods. Where the products are crystalline at room temperature, they are obtained by diluting the reaction mixture with water, acidifying, if necessary, and filtering.

It is, however, also possible to work up the mixture, in the usual way, by diluting with water, shaking with a virtually water-immiscible organic solvent (such as toluene) separating off the organic phase, washing it with water and distilling off the organic solvent.

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants: dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures: dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Cryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds which can be used according to the invention, as such or in the form of their formulations, can also be employed, for combating weeds, as mixtures with known herbicides, finished formulations or tank mixing being possible. Mixtures with other known active compounds, such as fungicides, insecticides, acaricides, nematicides, bird repellents, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They are preferably applied before emergence of the plants, that is to say by the pre-emergence method. They can also be incorporated into the soil before sowing.

The amount of active compound used can vary within a substantial range. It depends essentially on the nature of the desired effect. In general, the amounts used are between 0.05 and 10 kg of active compound per ha, preferably between 0.1 and 5 kg/ha.

The active compounds according to the invention, when used after emergence, exhibit growth-regulating properties.

The present invention also provides herbicidal compositions containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

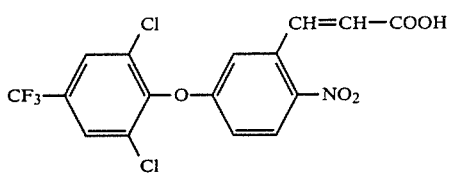

270 g of 5-(2,6-dichloro-4-trifluoromethylphenoxy)-2-nitro-benzaldehyde and 6 g of piperidine were added, at 25° C., to 89.5 g of malonic acid in 570 ml of pyridine. The reaction mixture was stirred for 5 hours at 85° to 90° C. and was then heated for 90 minutes under reflux, after which it was poured onto water, the mixture was acidified with hydrochloric acid and the product was filtered off. The crystalline product was recrystallized from n-butanol. 200 g (66% of theory) of 3-(5-(2,6-dichloro-4-trifluoromethyl-phenoxy)-2-nitrophenyl)-propenoic acid, of melting point 192° C., were obtained in the form of yellow crystals.

The compounds of the formula (I) listed in the examples which follow were also prepared in accordance with the method described in Example 1:

EXAMPLE 2

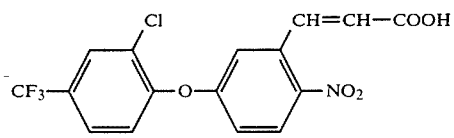

Melting point: 120° C.

EXAMPLE 3

Using cyanoacetic acid:

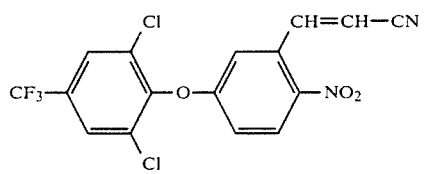

Melting point: 142° C.

EXAMPLE 4

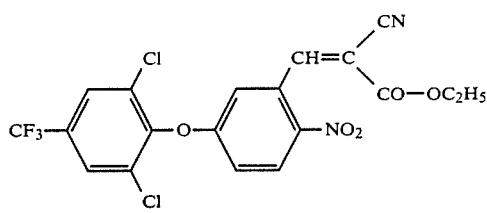

19 g of 5-(2,6-dichloro-4-trifluoromethylphenoxy)-2-nitro-benzaldehyde, 5.7 g of ethyl cyanoacetate, 0.6 g of acetic acid, 0.3 g of piperidine and 120 ml of toluene were mixed and heated to the boil for 6 hours under a water separator. 200 ml of toluene was then added and the organic phase was washed with water. The solvent was distilled from the organic phase and the residue was caused to crystallise by digestion with methanol. 12.5 g (53% of theory) of ethyl 2-cyano-3-(5-(2,6-dichloro-4-trifluoromethylphenoxy)-2-nitro-phenyl)-propenoate, of melting point 99° C., were obtained in the form of pale yellow crystals.

The compounds of the formula (I) listed in the examples which follow were also prepared in accordance with the method described in Example 4:

EXAMPLE 5

Using malodinitrile:

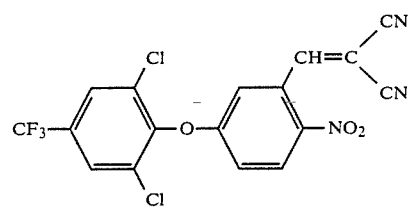

Melting point: 114° C.

EXAMPLE 6

Using methyl cyanoacetate:

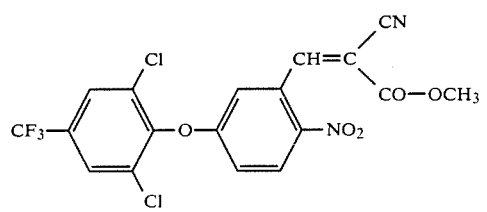

Melting point: 148° C.

EXAMPLE 7

Again using methyl cyanoacetate but with another aldehyde:

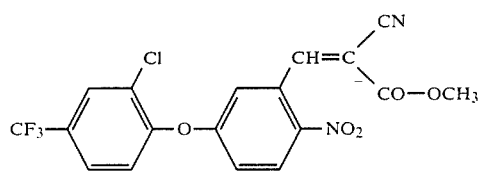

Highly viscous oil.

EXAMPLE 8

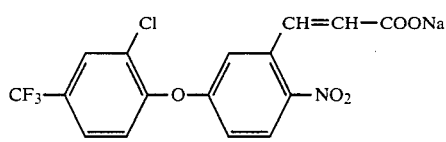 (8)

2.2 g of 3-(5-(2-chloro-4-trifluoromethylphenoxy)-2-nitro-phenyl)-propenoic acid (compound (2)) were stirred with 50 ml of methanol and 0.31 g of sodium methylate until a solution was formed; the solvent was then distilled off. 1.95 g (84% of theory) of sodium 3-(5-(2-chloro-4-trifluoromethyl-phenoxy)-2-nitro-phenyl) -propenoate, melting with decomposition at 230°–240° C., were obtained as the residue.

EXAMPLE 9

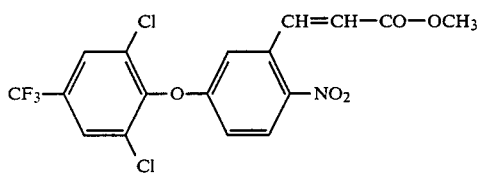 (9)

42.2 g of 3-(5-(2,6-dichloro-4-trifluoromethylphenoxy)-2-nitro-phenyl)-propenoic acid (compound (1)) were introduced into 120 ml of acetone and 18.7 g of diazabicycloundecene (DBU) were added, at 20° C. After 30 minutes, 35 g of methyl iodide were added dropwise. The reaction mixture was stirred for 15 hours at 50° to 60° C. and was diluted with water and methylene chloride; the organic phase was extracted by shaking with dilute sodium hydroxide solution and then with dilute hydrochloric acid, and was washed with water, dried and filtered. The solvent was distilled off the filtrate, and the residue was digested with ligroin and filtered off.

20.5 g (47% of theory) of methyl 3-(5-(2,6-dichloro-4-trifluoromethyl-phenoxy)-2-nitro-phenyl)-propenoate, of melting point 90° C., were obtained.

The compounds of the formula (I) listed in the examples which follow were also prepared in accordance with the method described in Example 9:

EXAMPLE 10

Using 2-iodopropane:

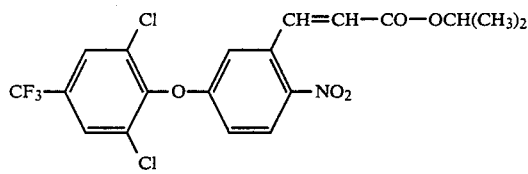 (10)

Melting point: 102° C.

EXAMPLE 11

Using ethyl iodide

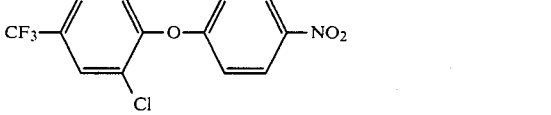 (11)

Melting point: 86° C.

PREPARATION OF STARTING MATERIALS

EXAMPLE 12

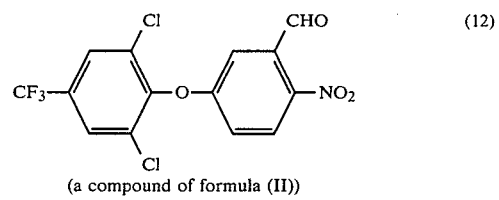 (12)

(a compound of formula (II))

Process variant (a):

A mixture of 12.1 g of 5-(2,6-dichloro-4-trifluoromethyl-phenoxy)-2-nitro-benzaldehyde-diacetacylal, 40 ml of methanol, 30 ml of water and 7 ml of 4% strength aqueous sodium hydroxide solution was stirred for 90 minutes at 40° C. and was then poured into water, and the product was filtered off. 9.0 g (95% of theory) of 5-(2,6-dichloro-4-trifluoromethyl-phenoxy)-2-nitro-benzaldehyde, of melting point 115° C., were obtained.

EXAMPLE 13

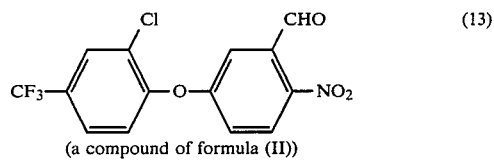 (13)

(a compound of formula (II))

Process variant (b):

100 g of 5-(2-chloro-4-trifluoromethyl-phenoxy)-2-nitrobenzyl alcohol were dissolved in 370 ml of nitromethane. A mixture of 86.4 g of 65% strength nitric acid and 43.2 g of water was then added dropwise in the course of 90 minutes to this solution, at 60° to 65° C., and the mixture was stirred for 8 hours at 60° to 65° C. It was then diluted with 4 liters of water, and the product was filtered off. 50.2 g (50% of theory) of 5-(2-chloro-4-trifluoromethyl-phenoxy)-2-nitro-benzaldehyde, of melting point 95° C., were obtained.

EXAMPLE 14

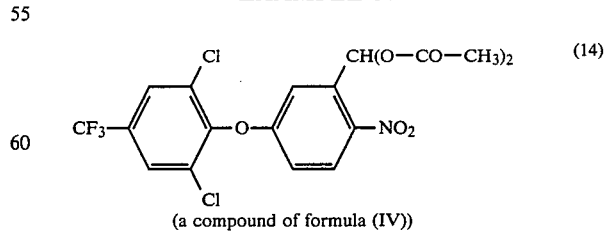 (14)

(a compound of formula (IV))

34 g of 3-(2,6-dichloro-4-trifluoromethyl-phenoxy)-benzaldehyde and 42.8 g of acetic anhydride were dissolved in 100 ml of methylene chloride and the solution was stirred for 1 hour at 40° C. When it had cooled to 20° C., 2 g of sulphuric acid were added. 10 g of 70% strength nitric acid were then added dropwise at 2° to 5° C. and the reaction mixture was stirred for 4 hours at 0° to 5° C. For working up, 1 liter of water was added, the methylene chloride was distilled off and the crystalline product was filtered off. 80 g of 5-(2,6-dichloro-4-trifluoromethyl-phenoxy)-2-nitro-benzaldehyde-diacetacylal, of melting point 132° C., were obtained.

EXAMPLE 15

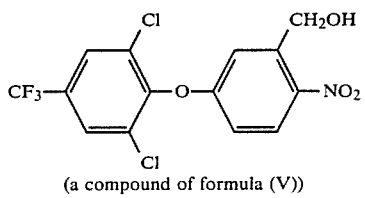

(a compound of formula (V))

A solution of 41.5 g of 5-(2,6-dichloro-4-trifluoromethyl-phenoxy)-2-nitro-benzoic acid chloride in 100 ml of diglyme was added to a mixture of 4.2 g of sodium boranate and 60 ml of diglyme at $-5°$ to $-10°$ C. The reaction mixture was stirred for about 15 hours at room temperature, diluted with 1.2 liters of water and acidified with acetic acid, and the product was filtered off. 36 g (94% of theory) of 5-(2,6-dichloro-4-trifluoromethyl-phenoxy)-2-nitro-benzyl alcohol, of melting point 143° C., were obtained.

The compound shown in the example which follows was also prepared in accordance with the method described in Example 15:

EXAMPLE 16

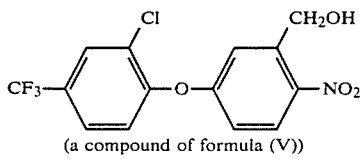

(a compound of formula (V))

Melting point 84° C.

EXAMPLE 17

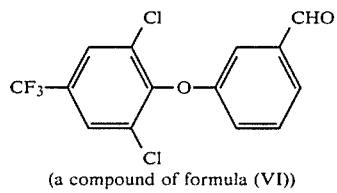

(a compound of formula (VI))

A mixture of 123 g of potassium hydroxide, 122 g of 3-hydroxy-benzaldehyde and 1 of methanol was stirred until a solution formed. The methanol was then carefully distilled off in vacuo. The residue was dissolved in 1.8 liters of dimethylsulphoxide. 300 ml of toluene were added and slowly distilled off again. At the same time, 536 g of 3,4,5-trichloro-benzotrifluoride were added dropwise. The reaction mixture was then stirred for 9 hours at 90° to 95° C. Thereafter the solvent was distilled off in vacuo and the residue was stirred with 1.2 liters of toluene and filtered off. The filtrate was washed with alkali and then until neutral, and was concentrated. 430 g (64% of theory) of 3-(2,6-dichloro-4-trifluoromethylphenoxy)-benzaldehyde, of melting point 54° C., were obtained.

EXAMPLE 18

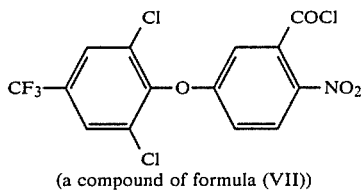

(a compound of formula (VII))

79.2 g of 5-(2,6-dichloro-4-trifluoromethyl-phenoxy)-2-nitro-benzoic acid and 0.5 ml of dimethylformamide were introduced into 150 ml of 1,2-dichloro-ethane. 28.6 g of thionyl chloride were added dropwise at 60° to 65° C. and the mixture was heated under reflux for 1 hour. The solution was clarified with active charcoal and filtered through kieselguhr. The mother liquor was concentrated and the residue was recrystallized from cyclohexane. 65.1 g (79% of theory) of 5-(2,6-dichloro-4-trifluoromethylphenoxy)-2-nitro-benzoic acid chloride, of melting point 95° C., were obtained.

The compound shown in the example which follows was also prepared in accordance with the method described in Example 18.

EXAMPLE 19

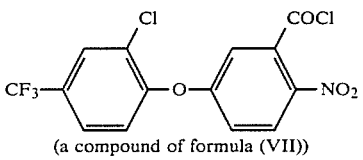

(a compound of formula (VII))

Melting point 61° C.

The herbicidal activity of the compounds of this invention is illustrated by the following examples wherein the compounds according to the present invention are each identified by the number (given in brackets) of the corresponding preparative example.

EXAMPLE 20

Pre-emergence test

Solvent: 5 parts by weight of acetone

Emulsifier: 1 part by weight of alkylaryl polyglycol ether

To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. The figures denoted:

0% = no action (like untreated control)

100% = total destruction

In this test, active compounds (1), (2) and (8) exhibited a very good selective herbicidal activity.

EXAMPLE 21

Post-emergence test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Test plants which had a height of 5 to 15 cm were sprayed with the preparation of the active compound in such a way as to apply the amounts of active compound per unit area which were prescribed. The concentration of the spray liquor was so chosen that the particular amounts of active compound desired were applied in 2,000 liters of water/ha. After 3 weeks, the degree of damage to the plants was rated in % damage in comparison to the development of the untreated control. The figures denoted:

0% = no action (like untreated control)
(100% = total destruction

In this test, active compounds (1), (2) and (8) exhibited a very good herbicidal activity.

It will be understood that the specification and examples are illustrative but not limitative of the present invention and that other embodiments within the spirit and scope of the invention will suggest themselves to those skilled in the art.

We claim:

1. A phenoxybenzene derivative of the formula

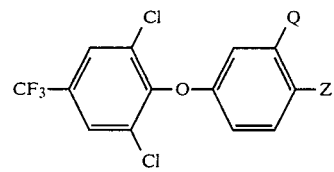

in which
Q represents —CH$_2$OH and Z represents NO$_2$, or
Q represents CHO and Z represents hydrogen.

2. A phenoxybenzyl alcohol according to claim 1 of the formula

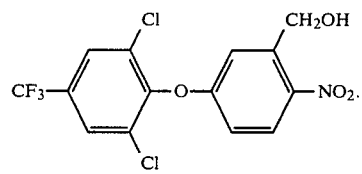

3. A phenoxybenzaldehyde according to claim 1 of the formula

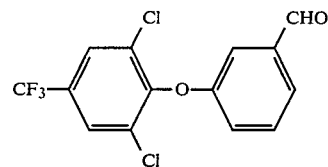

* * * * *